United States Patent [19]

Blaschke et al.

[11] Patent Number: 4,584,121
[45] Date of Patent: Apr. 22, 1986

[54] AMPHOTERIC COMPOUNDS, MIXTURES CONTAINING THESE COMPOUNDS FOR DISINFECTANT CLEANING, AND PROCESSES FOR THE PREPARATION OF THESE COMPOUNDS AND MIXTURES

[75] Inventors: Günter Blaschke, Winhöring; Adolf May, Hofheim am Taunus; Hans-Walter Bücking, Kelkheim; Karl H. Wallhäusser, Hofheim am Taunus, all of Fed. Rep. of Germany

[73] Assignee: Hoechst Akteingesellschaft, Fed. Rep. of Germany

[21] Appl. No.: 686,729

[22] Filed: Dec. 27, 1984

[30] Foreign Application Priority Data

Dec. 30, 1983 [DE] Fed. Rep. of Germany ....... 3347534

[51] Int. Cl.$^4$ .......................... C11D 1/10; C11D 1/84; C11D 3/48
[52] U.S. Cl. ..................................... 252/106; 252/546; 260/501.11; 562/561; 562/565
[58] Field of Search ...................... 252/106, 527, 546; 260/501.11; 562/561, 565; 424/316, 319

[56] References Cited

U.S. PATENT DOCUMENTS 2,717,850  9/1955  Schmitz .......................... 252/546 X
3,490,743  1/1970  Schmitz ............................... 252/106
3,873,688  3/1975  Kalopissis et al. .................... 424/70

FOREIGN PATENT DOCUMENTS 1556469  12/1968  France .
13846    7/1965  Japan .
16350    7/1965  Japan .
48077    12/1970 Japan .

Primary Examiner—Prince E. Willis
Attorney, Agent, or Firm—Connolly and Hutz

[57] ABSTRACT

Amphoteric compounds of the formula

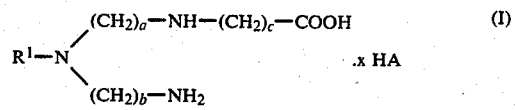

and their mixtures with compounds of the formula

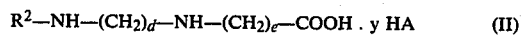

and, where appropriate, of the formula

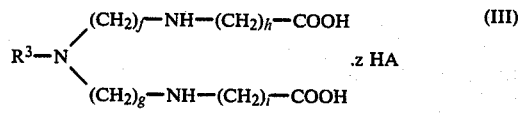

in which $R^1 = R^2 = R^3$ and is an alkyl or alkenyl radical having 8 to 22 carbon atoms; A is the anion of a mineral or carboxylic acid; a and b are 2 or 3; c is 1 or 2; x is 0, 1, 2 or 3; d is 3; e is 1 or 2; y is 0, 1 or 2; f and g are 2 or 3; h and i are 1 or 2; and z is 0, 1, 2 or 3, and processes for the preparation of these compounds and mixtures are described. They have microbicidal properties and are suitable as disinfectant cleaning agents.

12 Claims, No Drawings

AMPHOTERIC COMPOUNDS, MIXTURES CONTAINING THESE COMPOUNDS FOR DISINFECTANT CLEANING, AND PROCESSES FOR THE PREPARATION OF THESE COMPOUNDS AND MIXTURES

Amphoteric compounds of the alkylpoly[ethyleneamino]glycine type having the general formula R—NH($C_2H_4$NH)$_n$ $CH_2$—COOH (R=longish chain alkyl radical, n=1 or a multiple of 1) are known materials having microbicidal and algicidal actions, as are used, for example, for disinfection of the hands, for disinfection of hard surfaces and for protection against infections in the foodstuff and beverage industries. Compounds of the abovementioned type are prepared from alkylpoly[ethyleneamine] compounds, which in turn are normally obtained by reaction of alkyl halides with excess ethylenediamine, diethylenetriamine or triethylenetetraamine. The compounds thus resulting, of the alkylpoly[ethyleneamine] type, are then reacted with ω-halogenocarboxylic acids or terminally unsaturated alkenecarboxylic acids or their salts. The preparation of compounds of this type is described in, for example, German Pat. No. 812,105, German Pat. No. 947,972 or German Pat. No. 856,042. However, the preparation of these amphoteric compounds, which are intrinsically very effective as microbicides, is associated with considerable disadvantages. In order to obtain monosubstituted compounds of the alkylpoly[ethyleneamine] type (that is to say avoiding further addition of alkyl halide onto the primary and secondary amino groups of the polyalkyleneamine which are still present), it is necessary for the alkyl halides to be reacted with a 4- to 5-fold molar excess of the abovementioned polyamines. Following this reaction, the excess amine must be removed by distillation. In spite of the large excess of polyalkyleneamine, nevertheless dialkyl, trialkyl and tetraalkyl substituted derivatives of these polyalkyleneamines are produced as byproducts. These byproducts, which are present in considerable amounts, give rise, after conversion into the amphoteric compound using the abovementioned halogenocarboxylic acids or terminally unsaturated alkenecarboxylic acids, to cloudiness and precipitation, and thus act to reduce the quality. Likewise, the abovementioned removal of the polyalkyleneamines by distillation leads to dark-colored products whose quality is equally unsatisfactory. For this reason, in general, it is necessary for the desired alkylpolyaminoethylene also to be distilled before conversion into the amphoteric compound.

Furthermore, in order to avoid this elaborate preparation and purification of the abovementioned amphoteric compounds, the use of alkylpoly[trimethyleneamino]-glycines of the formula R—NH($CH_2CH_2CH_2$NH)$_n$$CH_2$COOH as microbicides has already been described (see, for example, German Pat. No. 1,041,627). The precursors of this class of amphoteric compounds, namely polyamines of the alkylpoly[trimethyleneamine] type are prepared by addition of acrylonitrile onto primary alkylamines, followed by catalytic hydrogenation, using Raney nickel and hydrogen, of the alkylaminopropionitriles thus produced. This addition of acrylonitrile can be repeated several times. Reaction of the finally obtained hydrogenation products with ω-halogenocarboxylic acids or terminally unsaturated carboxylic acids in the manner described above then leads to the abovementioned type of alkylpoly[trimethyleneamino]glycines, whose microbicidal effect approximately corresponds to that of the alkylpoly[ethyleneamino]glycines. However, the lengthening of the polyaminoalkylene chain, in each case by one $CH_2$ unit, has a disadvantageous effect on the solubility of these amphoteric compounds. This poorer solubility can lead to precipitation in aqueous formulations. In addition, the multistep synthesis (because of the multistep addition of acrylonitrile) is relatively elaborate.

Thus, there is a need for compounds which have a disinfectant action and which have the advantages of this class of amphoteric compounds but, nevertheless, do not have the abovementioned disadvantages.

This need is taken account of according to the present invention by amphoteric compounds of the formula

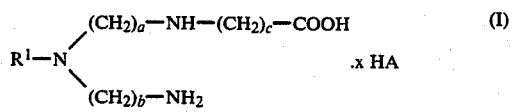

in which
$R^1$ is an alkyl or alkenyl radical having 8 to 22 carbon atoms;
A is the anion of a mineral or carboxylic acid;
a and b, independently of one another, can assume values of 2 or 3;
c can assume values of 1 or 2; and
x is 0 or can assume integral values from 1 to 3.

In these compounds of the formula I, $R^1$ is preferably an alkyl radical having 8 to 14 carbon atoms, and a and b have the value 3. A is preferably Cl, Br, hydrogen phosphate, acetate, lactate or glycolate.

These amphoteric compounds of the formula I, according to the invention, are very readily soluble in water, and they even show slightly improved microbicidal properties compared with the abovementioned known amphoteric compounds. They are readily accessible, without the formation of byproducts, by the route described in the following text. Purification operations on the final product of the formula I obtained or on intermediates are unnecessary.

In these compounds of the formula I, according to the invention, the radical $R^1$ has 8 to 22 carbon atoms, it can be saturated or unsaturated with 1 to 3 olefinic double bonds, and it can be straight-chain or branched. These alkyl or alkenyl radicals, which are derived from the primary starting amine in the preparation of the compounds of the formula I according to the invention, are frequently mixtures or chain sections, preferably with the chain distribution of the radicals of natural fatty acids, such as, in particular, of coconut, tallow or palm kernel fatty acid, from which these starting amines are obtained by the route of nitrile hydrogenation or of ammonolysis of the corresponding fatty alcohols. Apart from fatty alcohols, the alcohols used for the preparation of the primary amines by ammonolysis can be those having straight or branched chains from the Ziegler process (ethylene synthesis alcohols) or from the oxo synthesis.

For the preparation of the compounds of the formula I, according to the invention, first a primary amine of this type, of the formula $R^1NH_2$ (IV) in which $R^1$ has the abovementioned meaning, is reacted, in a dicyanoalkylation reaction, with 2 moles of at least one reactive nitrile having 2 or 3 carbon atoms (including the CN group) to give a compound of the general formula

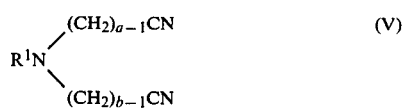

in which $R^1$, a and b have the abovementioned meaning. This reaction is known, for example from U.S. Pat. No. 3,028,415. It can be carried out with both acid and basic catalysis, using solvents, such as water or shortchain alcohols, under atmospheric pressure or under elevated pressure, continuously or discontinuously. Acid catalysts which are mentioned are acetic acid, phosphoric acid, hydrochloric acid and other mineral acids (U.S. Pat. No. 3,615,797, U.S. Pat. No. 3,028,415, German Offenlegungsschrift No. 1,941,913), and basic catalysts which have been recommended are sodium or potassium hydroxide, alkali metal alcoholates, trimethylbenzylammonium hydroxide and morpholine (Kirk-Othmer, Encyclopedia of Chemical Technology, 1965, Volume 6, pages 634 et seq.; H. A. Bruson "Cyanoethylation", Organic Reactions 5, 1949, pages 79 et seq., published by John Wiley and Sons, New York). Water or lower alcohols, such as methanol, ethanol, isopropanol or mixtures of these are added in proportions of from 1 to 20% by weight as cocatalysts or as solubilizers. The dicyanoalkylation is carried out under atmospheric pressure or slightly to moderately elevated pressure from 1 to 20 bar, where appropriate in the presence of an inert gas, and at temperatures of from 60° to 150° C. The cyanoalkylation agent, preferably acrylonitrile, chloroacetonitrile or ω-chloropropionitrile, is used in the stoichiometric amount or in an excess of up to 4-fold.

Subsequently, the dicyanoalkylation product thus obtained (V) is reduced in the presence of hydrogen to give a compound of the formula

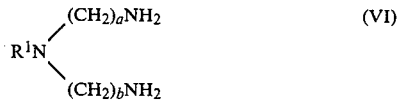

in which again $R^1$, a and b have the abovementioned meaning.

The amine of the formula VI obtained in this reduction is dispersed in water and reacted with a ω-halogenocarboxylic acid of the formula $X(CH_2)_cCOOH$ (VII), in which X is halogen, preferably Cl or Br, and c has the meaning mentioned in formula I, such as, for example, with ω-halogenopropionic acid, halogenoacetic acid, or with acrylic acid, or with the alkali metal or alkaline earth metal salts, the esters or the nitriles which derive from the abovementioned carboxylic acids, and, where appropriate, in the case of the esters and nitriles, is hydrolyzed to give the free carboxylic acids and, where appropriate, is neutralized with mineral or carboxylic acids with formation of the salts. A molar ratio of amine of the formula VI: carboxylic acid or carboxylic acid derivative of 1:1 is maintained in the reaction. The reaction takes place at temperatures of 80° to 100° C. If the reaction is carried out with the abovementioned halogenocarboxylic acids, then the amphoteric compound results as the hydrohalide, from which the free amphoteric compound of the formula I (x=0) can be liberated by treatment with alkalis.

The amphoteric compounds of the formula I thus prepared according to the invention are microbicides having very good disinfectant properties, as can be seen from Table 2, and they can be obtained in aqueous formulations having a concentration of active compound of up to 50% by weight, and in alcoholic formulations having a concentration of active compound of up to 90% by weight, since they do not pass through a so-called gel phase (that is to say the condition of a highly viscous mixture which can no longer be stirred) on conversion of the polyamine into the amphoteric compound. This gel phase which otherwise occurs prevents the production of aqueous formulations having more than 30% by weight of active compound in the case of the compounds of the state of the art discussed above.

Surprisingly, it has also emerged that the compounds of the formula I according to the invention are also able to confer on the abovementioned known amphoteric compounds of the alkylpoly[trimethyleneamine] type, as are defined below in formula II, an improved solubility in water, and thus make the latter more suitable for use in disinfectant cleaning compositions. Mixtures of this type can, where appropriate, also contain—whether from the method of preparation or as components added to the mixture—a proportion of amphoteric compounds of the formula III defined below.

Thus, disinfectant cleaning compositions are also made available by this invention, these containing (a) 80 to 30 mol-% of an amphoteric compound of the formula I as claimed in claim 1, and (b) 20 to 70 mol-% of an amphoteric compound of the formula

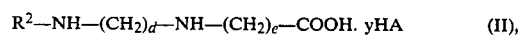

in which $R^2$ has one of the meanings mentioned for $R^1$ in formula I;

A is the anion of a mineral or carboxylic acid;

d is 3; e can assume values of 1 or 2, and y is 0 or can assume values of 1 or 2, it being possible for 0 to 50% of the molar amount of component (a) to be replaced by (c) an amphoteric compound of the formula

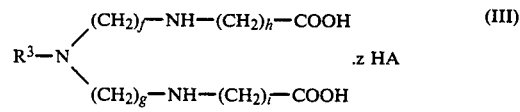

in which $R^3$ has one of the meanings mentioned for $R^1$ in formula I;

A is the anion of a mineral or carboxylic acid;

f and g, independently of one another, have values of 2 or 3;

h and i, independently of one another, have values of 1 or 2; and z is 0 or can assume integral values from 1 to 3.

Preferably, 0 to 25% of the molar amount of component (a) can be replaced by component (c).

As already indicated above, the compounds of the formula II which form the component (b) are known compounds which can be prepared by known processes. Equally, the compounds of the formula III, which can, where appropriate, be contained in the mixture as component (c), are known from Japanese Published Specification No. Sho-40-13,846 (see Chem. Abstracts 63, 1965, 17,982 g). Thus, the abovementioned mixtures which are used as disinfectant cleaners can be obtained by mixing the compounds of the formula I, according to the invention, with the separately prepared compounds of the formula II and, where appropriate, of the formula III in an appropriate ratio. In this case, every compound lying within the framework of the above definition of the substituents of the formula I can be used.

However, it is also possible to produce mixtures of this type by a variant of the preparation process described above for the compounds of the formula I according to the invention. In a case of this type, the starting amines $R^1NH_2$ of the formula IV are reacted with a reactive nitrile having 3 carbon atoms (including the CN group), that is to say preferably with acrylonitrile or with ω-chloropropionitrile, namely in an amount of less than 2 and more than 1 mole per mole of the abovementioned starting amino of the formula IV. Thus, in this instance, dicyanoalkylation is accompanied by monocyanoalkylation, which leads to the abovementioned mixture. Preferably, 1.8 to 1.3 moles of the abovementioned nitriles are reacted with 1 mole of the starting amine.

The resulting mixture of nitrile and dinitrile is then reduced in the manner described above, and is converted into the corresponding mixture of amphoteric compounds of the formula I' and II', in which a, b and d are 3. Before the conversion, the content of tertiary and secondary amine nitrogen present in the mixture—corresponding to the content of the particular amines analogous to formulae I and II—is determined. If, in the conversion into the amphoteric compound using ω-halogenocarboxylic acids, their abovementioned derivatives, or using acrylic acid, 1 mole-equivalent of the abovementioned acids or acid derivatives is used per 1 mole-equivalent of secondary and per 1 mole-equivalent of tertiary amine nitrogen, then the abovementioned mixture of compounds of the formulae I' and II' is obtained. If 1 mole-equivalent of the abovementioned acids is used per 1 mole-equivalent of secondary amine nitrogen, but the proportion of these acids per 1 mole-equivalent of tertiary amine nitrogen is increased to more than 1 mole-equivalent, it being possible for this proportion to be up to 1.5, preferably up to 1.25, mole-equivalent, then the compounds of the formula I' in the abovementioned mixtures are partially, that is to say up to 50%, preferably up to 25%, of their molar amount, replaced by compounds of the formula III', in which h and i are 3.

It is also possible to add compounds of the abovementioned formula I in which the indices a and b are 2 to mixtures of this type which have been synthesized in the manner described. Furthermore, it is possible to admix other known compounds having disinfectant and cleansing actions with the compounds of the formula I, according to the invention, or the disinfectant cleaning mixtures which are described above in detail. Examples of these are quaternary ammonium salts having 1 to 2 longish fatty alkyl radicals and 1 or 2 short-chain alkyl radicals, one of which can also be a benzyl radical. Furthermore, these are compounds of the formula

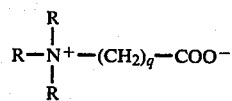

where, in this formula, one of the radicals R can also be $R-CO-NH-(CH_2)_3-$, while the remaining, or all, radicals R are alkyl groups, and q is 1 or 2.

The compounds of the formula I, according to the invention, and their mixtures are highly effective microbicides having very good bactericidal and algicidal actions. Their solubility in water is excellent, and they can be transported and marketed in the form of highly concentrated formulations in water or alcohols, or their mixtures, containing up to 90% by weight of active compound, these concentrates nevertheless being liquid at room temperature. The minimum content (preferably at least 10% by weight) of formulations of this type is not critical, since such highly concentrated formulations can, before use, be diluted without difficulty to the desired content of active compound using water and/or alcohol. They are particularly suitably for disinfection of the hands and for the disinfection of articles having hard surfaces, that is to say, for example, medical and dental instruments.

The compounds of the formula I, according to the invention, and the abovementioned mixtures can also be used as microbicidal additives in the formulation of cleansing agents, combined with customary anionic, nonionic, cationic and amphoteric surfactants. Examples of anionic surfactants suitable for this are soaps, fatty alcohol sulfates, alkyl ether sulfates, fatty acid condensation products, such as taurides, methyltaurides, sarcosides, also α-olefinsulfonates, hydroxyalkanesulsulfonates, secondary alkanesulfonates, amide ether sulfates or alkylbenzenesulfonates. Examples of nonionic surfactants which can be used are polyglycol monoalkyl ethers and monoesters, amine oxides and ethylene oxide/propylene oxide condensation products. In addition, combination with other amphoteric surfactants, such as alkylbetaines, alkylamidobetaines, imidazoline derivatives or sulfobetaines is also possible. Finally, the compounds of the Formula I, according to the invention, can also be used in mixtures with cationic surfactants, such as cetyltrimethylammonium chloride, cetyltrimethylammonium bromide, cetyldimethylbenzylammonium chloride, didecyldimethylammonium chloride, pentaoxyethylstearylammonium chloride, quaternized ether amines or polymeric quaternary ammonium compounds. Nonionic surfactants are preferred. Other additives which are otherwise customarily used in cleansing agents can, where appropriate, be combined with the compounds of the formula I according to the invention. Examples of these are compounds which increase or reduce the viscosity, such as cellulose ethers, electrolytes, such as, for example, sodium chloride or ammonium chloride, fatty acid polyglycol esters, alkanolamides, magnesium aluminum silicates, polyglycols, glycerol and ethanol. Furthermore, in processing to products in the form of powders, customarily used fillers and vehicles, such as highly disperse amorphous silica, sodium sulfate, magnesium aluminum silicate, starch derivatives and the like can be used. Other customary additives are bleaching agents, chlorine donors, chelateforming agents and, where appropriate, plastics dispersions.

Cleaning agents of this type normally contain the compounds of the formula I, according to the invention, or their mixtures in an amount of from 1 to 40, preferably from 10 to 20, % by weight, it also being possible for larger or smaller amounts than these to be contained for specific application purposes.

The examples which follow are intended to illustrate the invention in detail:

PREPARATION OF THE STARTING AMINES OF THE FORMULA VI OR OF THE AMINE MIXTURES VI'

Example A 670 g of technical laurylamine (composition in respect of the radicals R: $C_{12}$ 73% by weight; $C_{14}$ 27% by weight; 3.5 moles), 68 g of water, 34 g of methanol and 14 g of concentrated acetic acid are heated to 60° C. in a 2-liter four-necked flask with reflux condenser, thermometer, stirrer and metering vessel. 373 g (7.03 moles) of acrylonitrile are added dropwise within one hour, and the mixture is stirred at 75° C. under reflux for a further 24 h. It is then neutralized with 13 g of NaOH and 120 g of water, the wash water is separated off, and the remaining water and solvent are removed from the product is vacuo. 1,000 g of the appropriate laurylaminodipropionitrile are obtained with an amine value of 33.9 and a tertiary amine content of 96.9%. The amine value (AV) and the content of tertiary nitrogen are determined by titration with 0.1N $HClO_4$ in glacial acetic acid or acetic anhydride.

A 5-liter autoclave is charged with 2,020 g of the laurylaminodipropionitrile thus obtained, 3 g of supported cobalt catalyst (support: kieselguhr) and 300 ml of liquid ammonia. Hydrogenation is carried out under 150 to 180 bar of $H_2$ and at 110° to 140° C. within 3 hours. After removal of the catalyst by filtration, 2,010 g of mixture VI' which is composed almost quantitatively of bis(3-aminopropyl)laurylamine with a very small amount of laurylaminotrimethyleneamine are obtained. It has the following characteristics:
AV=97.4
65.8% of primary amine groups
2.1% of secondary amino groups
32.1% of tertiary amine groups.

The determination of the amine value and of the amine distribution is carried out by titration with 0.2N isopropanolic HCl in anhydrous medium. The amine distribution is determined by blocking the basic amine nitrogen with salicylaldehyde (primary N) or phenyl isothiocyanate (primary and secondary N).

Example B 670 g of the laurylamine from Example A (3.5 moles) are reacted with 335 g (6.3 moles) of acrylonitrile and then hydrogenated, as already described in Example A. The amine mixture VI', composed of 81.8% by weight of bis(3-aminopropyl)laurylamine and 18.2% by weight of laurylaminotrimethyleneamine, has the following characteristics:
AV=95.0
63.3% of primary amino groups
9.1% of secondary amino groups
27.6% of tertiary amino groups.

Example C 670 g of the laurylamine from Example A (3.5 moles) are reacted with 248 g (4.7 moles) of acrylonitrile and then hydrogenated, as described in Example A. The amine mixture VI', composed of 34.6% by weight of bis(3-aminopropyl)laurylamine and 65.4% by weight of laurylaminotrimethyleneamine, has the following characteristics:
AV=86.4
55.5% of primary amino groups
32.7% of secondary amino groups
11.8% of tertiary amino groups.

PREPARATION OF THE COMPOUNDS AND MIXTURES ACCORDING TO THE INVENTION

Example 1

308 g of amine from Example (A) and 829 g of water are introduced into a 2-liter reaction vessel and, with stirring, heated to 90° C. 99.2 g of chloroacetic acid are added at this temperature within 1 h. Reaction is then allowed to continue for a further 5 h at 95° C. The product is analyzed by HPLC.

Example 2

308 g of amine from Example (A) are introduced into 210 g of isopropanol in a 2-liter reaction vessel and, with stirring, heated to 60° C. 88.7 g of methyl acrylate are added dropwise at this temperature within 3 h. The mixture is then stirred a further 5 h at 60° C. The addition compound is converted into the corresponding sodium salt by addition of 275 g of 15% by weight aqueous sodium hydroxide solution. 50 g of solvent are removed by distillation at 50° C. under waterpump vacuum in order to remove methanol. The solids content is adjusted to 50% by weight with water. The product is analyzed by HPLC.

Example 3

295.2 g of amine from Example (B) and 843.2 g of water are introduced into a 2-liter reaction vessel and, with stirring, heated to 90° C. 99.2 g of chloroacetic acid are added at this temperature within 1 h, and reaction is allowed to continue for a further 5 h at 95° C. The product is analyzed by HPLC.

Example 4

295.2 g of amine from Example (B) and 825 g of water are introduced into a 2-liter reaction vessel and, with stirring, heated to 90° C. 118.1 g of chloroacetic acid are added at this temperature with 1 h, and reaction is allowed to continue for a further 5 h at 95° C. The product is analyzed by HPLC.

Example 5

410.3 g of amine from Example (C) and 1,178 g of water are introduced into a 2-liter reaction vessel and, with stirring, heated to 90° C. 142.8 g of chloroacetic acid are added at this temperature within 1 h, and stirring is then continued for a further 5 h at 95° C. The product is analyzed by HPLC.

Example 6

410.3 g of amine from Example (C) and 1,000 g of water are introduced into a 2-liter reaction vessel and, with stirring, heated to 90° C. 177.2 g of chloroacetic acid are added at this temperature within 1 h, and stirring is then continued for a further 5 h at 95° C. The product is analyzed by HPLC.

Examples 1 to 6 are summarized in Table 1:

The microbicidal action of the compounds and mixtures according to the invention are shown in Table 2

(μg of active compound/ml of water; contact times 24 and 48 h; room temperature). The figures given denote the minimum inhibitory concentrations for complete killing of the initial number of $10^6$ organisms per ml.

TABLE 1

| Example | Composition of the amine mixture VI' in moles | | Acid or acid derivative (moles) | Amphoteric compound I' (moles) | Amphoteric compound II' (moles) | Amphoteric compound III' (moles) |
|---|---|---|---|---|---|---|
| | Triamine | Diamine | | | | |
| 1 | 0.96 | 0.04 | 1.05 | 0.91 | 0.04 | 0.04 |
| 2 | 0.96 | 0.04 | 1.03 | 0.92 | 0.04 | 0.03 |
| 3 | 0.82 | 0.18 | 1.05 | 0.77 | 0.17 | 0.04 |
| 4 | 0.81 | 0.19 | 1.25 | 0.63 | 0.18 | 0.17 |
| 5 | 0.65 | 0.35 | 1.05 | 0.63 | 0.34 | 0.02 |
| 6 | 0.65 | 0.35 | 1.25 | 0.48 | 0.33 | 0.18 |

The products are analyzed by high-performance liquid chromatography (HPLC) using a reverse phase system (RP-18) under ion-pair conditions in a methanolic-aqueous system using a Hewlett-Packard 1082B liquid chromatograph.

TABLE 2

| Microorganisms | Product from Example 1 | | Product from Example 3 | | Product from Example 5 | |
|---|---|---|---|---|---|---|
| | 24 h | 48 h | 24 h | 48 h | 24 h | 48 h |
| Staphylococcus aureus | 125 | 62.5 | 250 | 62.5 | 125 | 62.5 |
| Escherichia coli | 62.5 | 7.8 | 62.5 | 15.6 | 125 | 15.6 |
| Pseudomonas aeruginosa | 31.2 | 15.6 | 31.2 | 7.6 | 62.5 | 15.6 |
| Proteus mirabilis | 125 | 31.2 | 31.2 | 15.6 | 125 | 31.2 |
| Candida albicans | 125 | 15.6 | 31.2 | 15.6 | 31.2 | 15.6 |
| Desulfovibrio desulfuricans 85 | 31.2 | 7.8 | 31.2 | 7.8 | 31.2 | 7.8 |
| Desulfovibrio desulfuricans 39 | 31.2 | 7.8 | 15.6 | 15.6 | 31.2 | 7.8 |
| Algicidal effect | 62.5 | | 31.2 | | 62.5 | |

We claim:

1. Amphoteric compounds of the formula $$R^1-N \begin{pmatrix} (CH_2)_a-NH-(CH_2)_c-COOH \\ (CH_2)_b-NH_2 \end{pmatrix} \cdot x\,HA \quad (I)$$

in which
$R^1$ is an alkyl or alkenyl radical having 8 to 22 carbon atoms;
A is the anion of a mineral or carboxylic acid;
a and b, independently of one another, are the numerical values 2 or 3;
c is a numerical value and is 1 or 2; and
x is a numerical value which is zero or an integer ranging from 1 to 3.

2. Amphoteric compounds of the formula I, as claimed in claim 1, wherein
$R^1$ denotes an alkyl radical having 8 to 14 carbon atoms, and
a and b have the value 3.

3. Disinfectant cleaning compositions which contain
(a) 80 to 30 mol-% of an amphoteric compound of the formula I as claimed in claim 1, and
(b) 20 to 70 mol-% of an amphoteric compound of the formula $$R^2-NH-(CH_2)_d-NH-(CH_2)_e-COOH \cdot yHA \quad (II)$$

in which
$R^2$ is an alkyl or alkenyl radical having 8 to 22 carbon atoms;
A is the anion of a mineral or carboxylic acid,
d is 3; e is the numerical value 1 or 2, and y to a numerical value which is zero, 1, or 2.

4. Disinfectant cleaning composition as claimed in claim 3, wherein from 0 to 50% of the molar quantity of component (a) is replaced by an amphoteric compound of the formula $$R^3-N \begin{pmatrix} (CH_2)_f-NH-(CH_2)_h-COOH \\ (CH_2)_g-NH-(CH_2)_i-COOH \end{pmatrix} \cdot z\,HA \quad (III)$$

in which
$R^3$ is an alkyl or alkenyl radical having 8 to 22 carbon atoms,
A is the anion of a mineral or carboxylic acid;
f and g, independently of one another, have values of 2 or 3;
h and i, independently or one another, have values of 1 or 2; and
Z is a numerical value from 0 to 3.

5. A process for the preparation of amphoteric compounds of the formula I as claimed in claim 1, in which first a primary amine of the formula $R^1NH_2$ (IV), in which $R^1$ has the meaning mentioned in formula I, is reacted with 2 moles of at least one reactive nitrile having 2 or 3 carbon atoms to give a compound of the formula $$R^1N \begin{pmatrix} (CH_2)_{a-1}CN \\ (CH_2)_{b-1}CN \end{pmatrix} \quad (V)$$

wherein a and b have the numerical values defined in claim 8, and the latter is reduced in the presence of hydrogen to give a compound of the formula $$R^1N \begin{pmatrix} (CH_2)_aNH_2 \\ (CH_2)_bNH_2 \end{pmatrix} \quad (VI)$$

said process further comprising reacting the compound of formula VI, in aqueous solution, with at least one ω-halogenocarboxylic acid of the formula $X(CH_2)_cCOOH$ (VII), or a nitrile or an ester thereof, in which X is halogen and c has the meaning mentioned in formula I, or with acrylic acid or an ester or nitrile thereof, or with an alkali metal or alkaline earth metal salt of said carboxylic acid of formula (VII) or of acrylic acid.

6. The process as claimed in claim 5, wherein the resulting product, if not already a carboxylic acid, is hydrolyzed to form the carboxylic acid.

7. The process as claimed in claim 6, wherein the resulting product is neutralized with a mineral or carboxylic acid or with alkali.

8. A process for the preparation of a mixture of (a') an amphoteric compound of the formula $$R^1-N\begin{matrix}(CH_2)_3-NH-(CH_2)_c-COOH\\ \\ (CH_2)_3-NH_2\end{matrix}\quad .xHA \qquad (I')$$

in which
  $R^1$ is an alkyl or alkenyl radical having 8 to 22 carbon atoms;
  A is the anion of a mineral or carboxylic acid;
  c is a numerical value which is 1 and 2; and
  x is an integer ranging from 1 to 3, and
(b') an amphoteric compound of the formula $$R^2-NH-(CH_2)_3-NH-(CH_2)_e-COOH.yHA \qquad (II')$$

in which
  $R^2$ is identical to $R^1$;
  A is the anion of a mineral or carboxylic acid;
  e is a numerical value which is 1 to 2; and
  y is a numerical value which is 1 or 2,
which comprises reacting a primary amine of the formula $R^1NH_2$,
  in which $R^1$ has the meaning mentioned in formula I, with less than 2 moles but more than 1 mole of a reactive nitrile having 3 carbon atoms, reducing in the presence of hydrogen to give a mixture VI' of the compounds of the formulae $$R^1N\begin{matrix}(CH_2)_3NH_2\\ \\ (CH_2)_3NH_2\end{matrix} \quad \text{and} \quad R^1N-(CH_2)_3-NH_2 \atop H$$

and then reacting this mixture, in aqueous solution, with 1 mole-equivalent of at least one ω-halogenocarboxylic acid of the formula $X(CH_2)_cCOOH$ (VII), or an ester or a nitrile thereof, in which X is halogen and c has the meaning mentioned in formula I, or with acrylic acid or an ester or nitrile thereof or with an alkali metal or alkaline earth metal salt of said carboxylic acid of formula (VII) or of acrylic acid, per mole-equivalent of tertiary amine nitrogen present, and also one mole-equivalent per mole-equivalent of secondary amine nitrogen present.

9. The process as claimed in claim 8, wherein the resulting product, if not already a carboxylic acid, is hydrolyzed to form the carboxylic acid.

10. The process as claimed in claim 9, wherein the resulting product is neutralized with a mineral or carboxylic acid or with alkali.

11. The process as claimed in claim 8 for the preparation of a mixture of the components (a'), (b') and another amphoteric compound of the formula $$R^3-N\begin{matrix}(CH_2)_3-NH-(CH_2)_h-COOH\\ \\ (CH_2)_3-NH-(CH_2)_i-COOH\end{matrix}\quad .zHA \qquad (III')$$

in which
  $R^3$ is identical to $R^1$;
  A is the anion of a mineral or carboxylic acid;
  h and i, independently of one another, are the numerical values 1 or 2; and
  z is an integer ranging from 1 to 3,
which comprises using, in the reaction with ω-halogenocarboxylic acids, acrylic acids or their said ester or nitrile derivatives, 1 mole-equivalent per mole-equivalent of the secondary amine nitrogen present, but using more than 1 mole-equivalent, but not more than 1.5 mole-equivalent, of the above-mentioned ω-halogenocarboxylic acid, acrylic acid or their said derivatives per mole-equivalent of the tertiary amine nitrogen present.

12. A method for disinfecting human hands or hard surfaces which comprises disinfecting with a solution containing an effective amount of a compound of formula I as claimed in claim 1.

* * * * *